US00PP10109P

United States Patent [19]

Trees

[11] Patent Number: Plant 10,109

[45] Date of Patent: Nov. 4, 1997

[54] NEW GUINEA IMPATIENS NAMED 'BFP-490 LIGHT PINK'

[75] Inventor: Scott C. Trees, Arroyo Grande, Calif.

[73] Assignee: Ball Horticultural Company, West Chicago, Ill.

[21] Appl. No.: 685,537

[22] Filed: Jul. 24, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis, L.L.P.

[57] ABSTRACT

A new and distinct New Guinea Impatiens cultivar named 'BFP-490 Light Pink' is provided. This new cultivar was the result of a controlled breeding program wherein the 'Cameo' cultivar U.S. Plant Pat. No. 8,316) was pollinated by a plant designated 'BFP-363' (non-patented in the United States). The new cultivar forms large light pink flowers that display an iridescent appearance. The foliage is medium green coloration with a pale red midrib. An attractive medium upright mounded growth habit is exhibited. The new cultivar can be readily distinguished from the 'Cameo' cultivar.

1 Drawing Sheet

SUMMARY OF THE INVENTION

The present invention comprises a new and distinctive Impatiens plant, botanically known as New Guinea Impatiens, and hereinafter is referred to by the cultivar name 'BFP-490 Light Pink'.

The new cultivar is the product of a planned breeding program. More specifically, the breeding program which resulted in the production of the new cultivar was carried out in a controlled environment during 1992 at Arroyo Grande, Calif. U.S.A. The female parent (i.e., the seed parent) was the 'Cameo' cultivar (U.S. Plant Pat. No. 8,316) which exhibits salmon-coral blossoms, and medium green foliage. The male parent (i.e., the pollen parent) was a plant designated 'BFP-363' (non-patented in the United States) which exhibits salmon-coral blooms and dark green foliage. The parentage of the new cultivar can be summarized as follows:

'Cameo'×'BFP-363'.

The seeds resulting from the above pollination were sown and plantlets were obtained which were physically and biologically different from each other. Selective study resulted in the identification of a single plant of the new cultivar. This plant initially was designated BFP-490.

It was found that the new cultivar of the present invention:

(a) exhibits attractive large light pink flowers,
(b) forms medium green foliage with a pale red midrib,
(c) exhibits a good basal branching character, and
(d) exhibits a medium upright growth habit.

Plants of the new cultivar can be grown close together in the greenhouse.

Asexual reproduction of the new cultivar by terminal or stem cuttings taken during 1993, at Arroyo Grande, Calif. U.S.A. has demonstrated that the characteristics of the new cultivar as herein described are firmly fixed and are retained through successive generations of such asexual propagation.

The 'BFP-490 Light Pink' cultivar has not been observed under all possible environmental conditions to date. Accordingly, it is possible that the phenotype may vary somewhat with variations in the environment, such as temperature, light intensity, and day length.

When the new cultivar of the present invention is compared to the parent 'Cameo' cultivar (U.S. Plant Pat. No. 8,316), it is found that the new cultivar exhibits larger flowers and a more compact growth habit.

Plants of the new cultivar are marketed under the CELEBRETTE trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill. U.S.A. The greenhouse temperature was maintained at approximately 72° F. during the day and approximately 65° F. during the night. The plants were in flower eight to nine weeks later when the observations described hereafter were taken.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant Description:

*Form.*—Basal branching.

*Habit of growth.*—Medium upright, and mounded. A mature plant commonly measures approximately 10 to 12 cm. in height and approximately 18 to 20 cm. in width. This compares to a height of approximately 15 to 23 cm. and a width of approximately 24 to 27 cm. for the parent 'Cameo' cultivar.

*Foliage.*—The configuration is elliptic with an acuminate apex and an acuminate base. The mature leaves of the new cultivar measure approximately 9.5 to 10 cm. in length x approximately 3.5 to 3.7 cm. in maximal width. The leaf margins are serrate (as illustrated). The mature foliage of new cultivar is Yellow-Green Group 147A with a pale red midrib of Red-Purple Group 63C and green veins, Green Group 139C (adaxial), and Yellow-Green Group 147B, with green veins (abaxial). This generally compares to Green Group 137A (adaxial) and Green Group 137D (abaxial) for the 'Cameo' cultivar. Under high light conditions the foliage of the 'Cameo' cultivar is Green Group 137A at the margins with variegation along the midrib of Yellow-Green Group 1A (adaxial) and Green Group 137D (abaxial).

Flower Description:

*Flowering Habit.*—Freely flowering.

*Natural flowering season.*—Throughout the year in a greenhouse environment.

*Flowers borne.*—Above foliage, arising from leaf axils.

*Flower color.*—The superior petal is Red Group 55A (adaxial). The inferior petals are Red Group 55A at the outer edge and generally fade to Red Group 55D and have attachment points of Red-Purple Group 63A (adaxial). The superior petal is Red-Purple Group 73D and Red Group 53A where the sepals are fused (abaxial). The inferior petals have a blush of Red-Purple Group 73B (abaxial). This compares to Red Group 51B with attachment points of Red Group 53D (adaxial) and Red Group 43C (abaxial) for the 'Cameo' cultivar.

*Quantity of Flowers.*—Approximately 5 to 7 per axil for the new cultivar. This compares to approximately 6 to 9 per stem for the 'Cameo' cultivar.

*Number of petals.*—Five, and overlapping.

*Petal shape.*—Heart-shaped, with the three upper petals having broad bases and the lower two petals having pointed bases.

*Flower size.*—Approximately 7 to 7.5 cm. in length and approximately 7 to 7.1 cm. in width. This can be compared to approximately 5.5 to 5.9 cm. in length and approximately 5.9 to 6.1 cm. in width for the parent 'Cameo' cultivar.

*Flower buds.*—Ellipsoidal in configuration, and generally covered with three sepals plus two rudimentary sepals fused into the under surface of the superior petal. A spur originating from the base of the inferior sepal is approximately 5.8 to 6 cm. in length on fully opened flowers which can be compared to approximately 5 cm. for the spur length of the 'Cameo' cultivar. The spur coloration is Red Group 53B for the new cultivar and Red Group 53D for the 'Cameo' cultivar.

*Reproductive Organs.*—The stamens generally are colorless with streaks of Red-Purple Group 63A. The anthers tend to be fused together forming one organ that surrounds the pistil. Commonly the anthers shed pollen prior to the stigma becoming receptive. The pollen coloration is Yellow-Orange Group 19C, and the ovary coloration is Yellow-Green Group 146B. This compares to a pollen coloration of Yellow-Orange Group 19D and an ovary coloration of Yellow-Green Group 144A for the 'Cameo' cultivar.

I claim:

1. A new and distinct cultivar of New Guinea Impatiens named 'BFP-490 Light Pink', substantially as herein shown and described, which:

(a) exhibits attractive large light pink flowers,
(b) forms medium green foliage with a pale red midrib,
(c) exhibits a good basal branching character, and
(d) exhibits a medium upright growth habit.

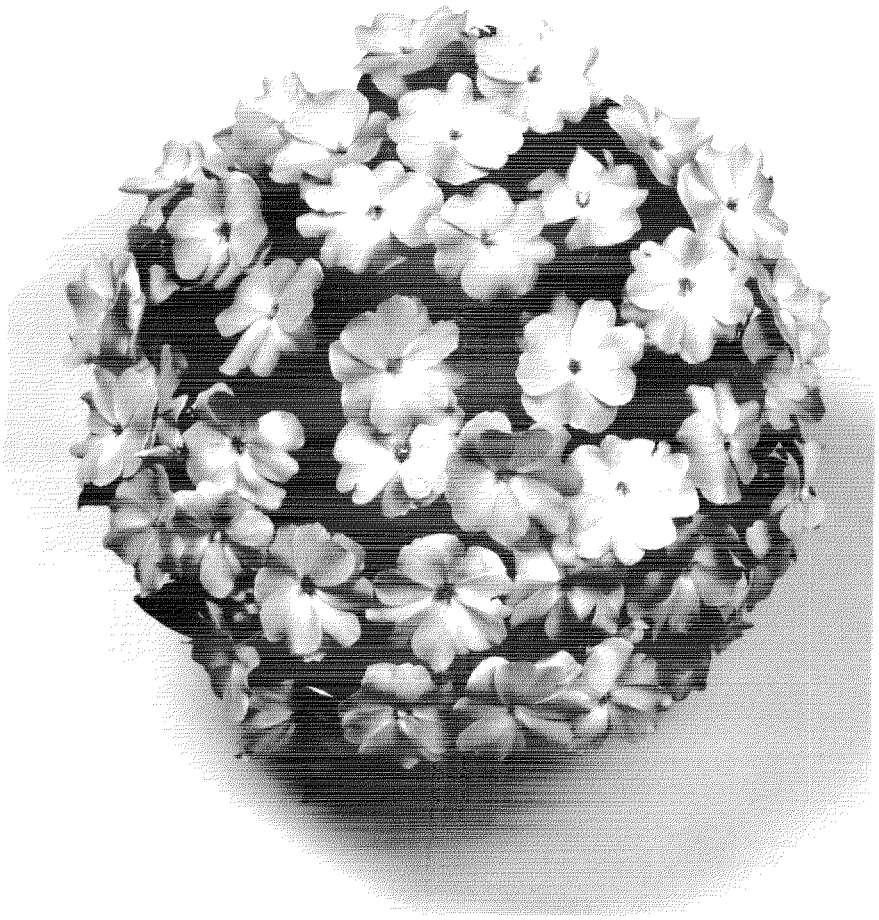

* * * * *